United States Patent
Chang et al.

(10) Patent No.: US 10,561,637 B2
(45) Date of Patent: Feb. 18, 2020

(54) METHODS FOR TREATING ANGIOGENESIS RELATED DISORDER

(71) Applicant: KAOHSIUNG MEDICAL UNIVERSITY, Kaohsiung (TW)

(72) Inventors: Hsun-Shuo Chang, Kaohsiung (TW); Ih-Sheng Chen, Kaohsiung (TW); Chien-Jou Peng, Hsinchu County (TW); Shih-Wei Wang, Taipei (TW); Chih-Hsin Tang, Taichung (TW)

(73) Assignee: KAOHSIUNG MEDICAL UNIVERSITY, Kaohsiung (TW)

( * ) Notice: Subject to any disclaimer, the term of this patent is extended or adjusted under 35 U.S.C. 154(b) by 0 days.

(21) Appl. No.: 15/905,835

(22) Filed: Feb. 27, 2018

(65) Prior Publication Data

US 2018/0353467 A1    Dec. 13, 2018

(30) Foreign Application Priority Data

Jun. 13, 2017   (TW) .............................. 106119658 A

(51) Int. Cl.
*A61K 31/365* (2006.01)
*A61K 36/185* (2006.01)

(52) U.S. Cl.
CPC .......... *A61K 31/365* (2013.01); *A61K 36/185* (2013.01)

(58) Field of Classification Search
CPC ................................................. A61K 31/365
See application file for complete search history.

(56) References Cited

PUBLICATIONS

Ismail et al., Ellagitannins in Cancer Chemoprevention and Therapy, 2016, Toxins, 8, 151, pp. 1-22 (Year: 2016).*
Sartippour et al., Ellagitannin-rich pomegranate extract inhibits angiogenesis in prostate cancer in vitro and in vivo, 2008, International Journal of Oncology, 32, pp. 475-480 (Year: 2008).*
Lansky et al., *Punica granatum* (pomegranate) and its potential for prevention and treatment of inflammation and cancer, 2007, Journal of Ethnopharmacology, 109, pp. 177-206 (Year: 2007).*
Seeram et al., In vitro antiproliferative, apoptotic and antioxidant activities of punicalagin, ellagic acid, and total pomegranate tannin extract are enhanced in combination with other polyphenols as found in pomegranate juice, 2005, Journal of Nutritional Biochemistry, 16, pp. 360-367 (Year: 2005).*
Xuemei Gu, Lei Cheng, Winghong L Chueng, Xinsheng Yao, Hongwei Liu, Guoqing Qi, and Ming Li (2006). Neovascularization of Ischemic Myocardium by Newly Isolated Tannins Prevents Cardiomyocyte Apoptosis and Improves Cardiac Function. Molecular Medicine 12(11-12), 275-283, 2006.
Sung-Jin Lee, Hwan Myung Lee, Seung-Taek Ji, Seung-Rock Lee, Woongchon Mar, Yong Song Gho (2004). 1,2,3,4,6-Penta-O-galloyl-beta-D-glucose blocks endothelial cell growth and tube formation through inhibition of VEGF Sinding to VEGF receptor. Cancer Letters 208(1) (2004) 89-94.
Loma M. Cryan, Lauren Bazinet, Kaiane A. Habeshian, Shugeng Cao, Jon Clardy, Kenneth A. Christensen, and Michael S. Rogers (2013). 1,2,3,4,6-penta-O-galloyl-β-D-glucopyranose (PGG) Inhibits Angiogenesis via Inhibition of CMG2. J Med Chem. Mar. 14, 2013; 56(5): 1940-1945. doi:10.1021/jm301558t.
Kenichi Miyamoto, Nobuharu Kishi, Ryozo Koshiura, Takashi Yoshida, Tsutomu Hatano, Takuo Okuda (1987). Relationship between the Structures and the Antitumor Activities of Tannins. Chemical and Pharmaceutical Bulletin 35(2), 814-822 (1987).
Ruth Niemetz and Georg G Gross (2003). Oxidation of pentagalloylglucose to the ellagitannin, tellimagrandin II, by a phenol oxidase from Tellima grandiflora leaves. Phytochemistry 62 (2003), 301-306.

* cited by examiner

*Primary Examiner* — Jeffrey S Lundgren
*Assistant Examiner* — Tori Strong
(74) *Attorney, Agent, or Firm* — Hannah Tien

(57) ABSTRACT

A method of treating a subject suffering from an angiogenesis-related disease, which is implemented by administering to the subject a pharmaceutical composition comprising a compound of formula I derived from *Mitella formosana* to inhibit the angiogenic function of endothelial progenitor cells.

4 Claims, 5 Drawing Sheets

METHODS FOR TREATING ANGIOGENESIS RELATED DISORDER

CROSS-REFERENCES TO RELATED APPLICATIONS

The present application claims priority to Taiwan Patent Application No, 106119658 filed Jun. 13, 2017, which is incorporated herein by reference in its entirety.

FIELD OF INVENTION

The present invention relates to a method for the treatment of angiogenesis-related diseases.

BACKGROUND OF INVENTION

Angiogenesis refers to the process of growing new blood vessels in close proximity to the existing ones. It is known that angiogenesis plays an important role in many physiological conditions, such as: embryonic development, reproduction, tissue repair and bone homeostasis. Under normal physiological mechanism, the resulting reaction can be stimulated by the promotion of angiogenic signals. For example, in the process of wound healing or menstrual cycle, there will be angiogenesis that is controllable and sustainable for about 1-2 weeks. However, pathological angiogenesis is not controllable by normal physiological mechanisms. The regulation of angiogenesis in human body plays an important homeostatic role. When angiogenesis is over progressed or expressed, it may cause obesity, psoriasis, preterm birth, endometriosis, diabetic retinopathy, age-related macular degeneration (AMD), rheumatoid arthritis and various inflammation related diseases, or acceleration of the deterioration and metastasis of tumors. In addition, when angiogenesis is insufficient, it may result in bleeding, stroke, cardiovascular disease, etc. due to defective coagulation, and even affect wound healing of patients.

In recent years, it has been found that there is a close relationship between angiogenesis and formation of tumors. When cancer cells form a tumor, the cancer cells themselves or the surrounding connective tissues will secrete angiogenic factors. These factors promote the following changes in endothelial cells: (1) decomposition and destruction of connective tissues around the tumor; (2) proliferation of endothelial cells; (3) migration of endothelial cells toward the location for the secretion of angiogenic factors; (4) re-combination of endothelial cells to form blood vessels. Angiogenesis is very important to tumor formation. When a tumor has developed to a certain size, it is necessary to generate new blood vessels for the tumor to effectively obtain nutrients and oxygen and remove waste. Angiogenesis is also important for tumor metastasis. Tumor cells must generate new blood vessels to enter the circulatory system, and then the tumor cells are transferred to other organs and tissues. After the tumor cells reach other organs and tissues, the tumor cells must generate new blood vessels in order to continue to grow in the organs and tissues. It has been confirmed that the growth or the metastasis of almost all solid tumors and vascular tumors rely on angiogenesis. Therefore, tumor formation or metastasis can be inhibited if angiogenesis can be suppressed.

Currently, there are about 19 angiogenesis inhibitors used clinically, and these drugs can be used to treat diseases including solid tumors, AMD, choroidal neovascularization, diabetic macular edema, diabetic retinopathy, ocular neoplasm, retinal venous occlusion, telangiectasis, and other related disease. Because angiogenesis is associated with a variety of diseases, the development of novel angiogenesis inhibitors is a very important research direction and development field for now and in the future.

Endothelial progenitor cells (EPCs) can be released from the bone marrow, move to ischemic tissues, and cooperate with existing blood vessels to facilitate neovascularization. EPCs are a group of cells with the ability to promote angiogenesis in the circulation, and it has been proved that late EPCs themselves can differentiate into endothelial cells, structure blood vessel formation and promote angiogenesis. Early EPCs are found to be able to release many angiogenic cytokines (such as VEGF and IL-8) to stimulate the function of peripheral endothelial cells, which in turn promote angiogenesis and vasculogenesis. Recently, it has been reported that EPCs can regulate the formation of early cancers and the subsequent cancer metastasis by activating "angiogenic switch." Many literatures have reported that EPCs can promote neovascularization in ocular hypoxic tissues, resulting in deterioration of age-related maculopathy. These studies show that EPCs play an important role in pathological angiogenesis, and EPC-based research and development will be a promising strategy to explore anti-angiogenic agents.

BRIEF DESCRIPTION OF DRAWINGS

FIG. 2A shows that under the described conditions and using the Sulforhodamine B (SRB) assay, PGG, tellimagrandin I and tellimagrandin II suppress the proliferation of EPCs in a concentration dependent manner at the 48th hour.

FIG. 3A shows, after human EPCs are treated with the described concentration of PGG and tellimagrandin II (5 and 10 μM) for 24 hours, the changes in tube formation recorded by a phase-contrast microscope.

SUMMARY OF INVENTION

The present invention is to provide a method of treating a subject suffering from an agniogenesis-related disease, comprising administering to the subject a pharmaceutical composition comprising a compound of formula I.

DETAILED DESCRIPTION OF THE INVENTION

Accordingly, the present invention is to provide a method of treating a subject suffering from an angiogenesis-related disease, comprising administering to the subject a pharmaceutical composition comprising a compound of formula I:

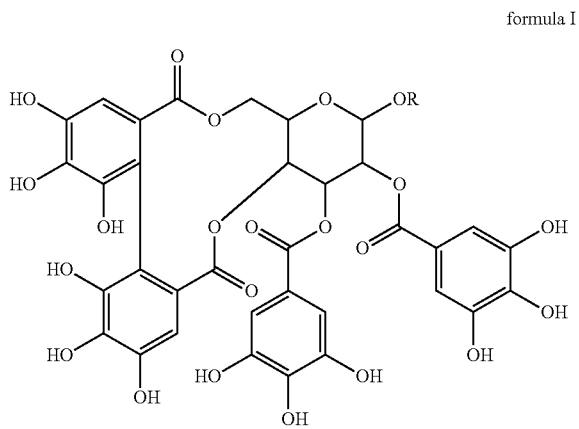

formula I wherein R is H or

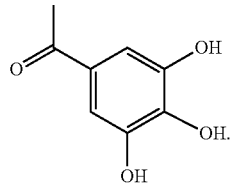

In a preferred embodiment of the present invention, the pharmaceutical composition treats the angiogenesis-related disease through the inhibition of neovascularization in vivo. In another preferred embodiment, the pharmaceutical composition inhibits neovascularization in vivo by inhibiting the angiogenic function of endothelial progenitor cells (EPCs).

In a preferred embodiment of the present invention, the compound of formula I is derived from the extract of *Mitella formosana*. In another preferred embodiment, the pharmaceutical composition further comprises at least one pharmaceutically acceptable carrier, adjuvant or excipient. The excipient(s) include, but are not limited to, inert diluents, granulating agents, disintegrants, binders, lubricants, frothing mixtures, dyes or sweeteners.

In the present invention, the angiogenesis-related disease (s) include, but are not limited to, various solid tumors, psoriasis, preterm birth, endometriosis, age related macular degeneration (AMD), choroidal neovascularization, diabetic macular edema, diabetic retinopathy, ocular neoplasm, retinal venous occlusion, telangiectasis, rheumatoid arthritis and many inflammation related diseases.

The examples below are non-limiting and are merely representative of various aspects and features of the present invention.

EXAMPLES

The extraction step of the compound of formula I

Figure 1:
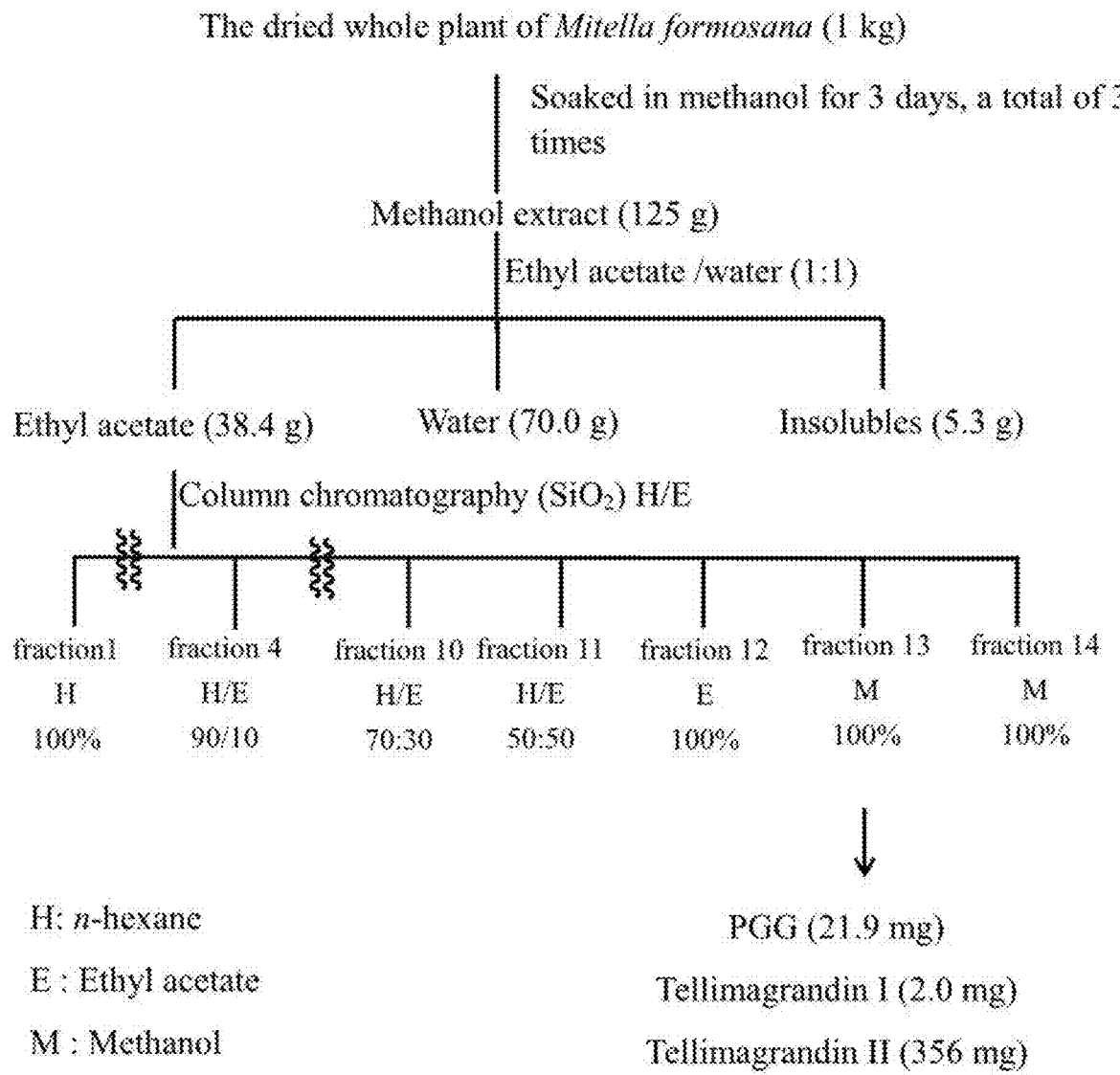
FIG. 1 illustrates the extraction step of the compound of formula I.

FIG. 1 shows the extraction step of the compound of formula I. The whole plant of *Mitella formosana* (1 kg) was washed and dried, and then soaked in methanol for 3 days at room temperature, this step was repeated 3 times. The resulting extract solution was concentrated under reduced pressure to obtain a methanol extract (125 g). The methanol extract was partitioned with ethyl acetate/water (1:1, v/v) to give an ethyl acetate layer (38.4 g), an aqueous layer (70 g) and insoluble material (5.3 g). The ethyl acetate layer was chromatographed with silica gel (MERCK®), RP-18 (MERCK®) and molecular sieves (SEPHADEX® LH-20; Pharmacia) as the stationary phase, and in coordination with medium pressure liquid chromatography (MPLC), recrystallization techniques and preparative TLC, PGG (21.9 mg), tellimagrandin I (2.0 mg) and tellimagrandin II (356 mg) were isolated and purified. The structure of PGG, tellimagrandin I and tellimagrandin II were determined by 1D, 2D-NMR spectroscopy and further confirmed by mass spectrometry, ultraviolet light analyzer, infrared light analyzer and optical rotation spectroscopy.

Figure 2A:
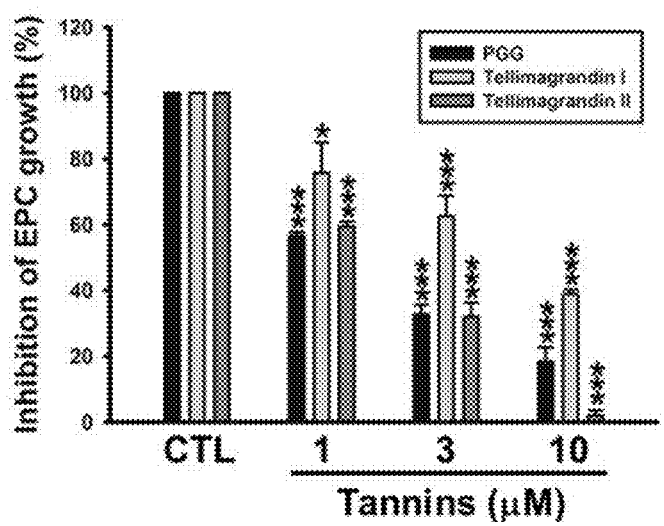
FIG. 2A shows the effect of 1,2,3,4,6-penta-O-galloyl-β-D-glucose (PGG), tellimagrandin I (T-I) and tellimagrandin II (T-II) on cell proliferation and tube formation in human EPCs.
Figure 2B:
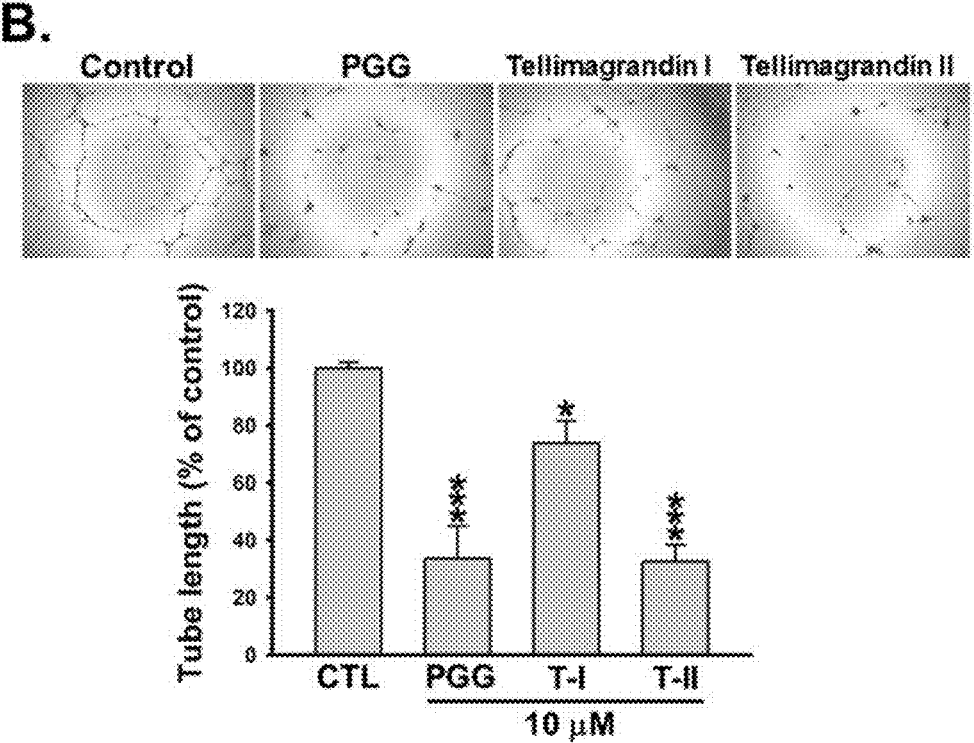
FIG. 2B shows inhibition of the formation of capillary-like structures of human EPCs at the 24 th hour by the described tannins (10 μM) and measured by using the tube formation assay. The data of five independent experiments are expressed as the mean±mean standard deviation. As compared with the control group, * means p<0.05; *** means p<0.001.
Figure 3A:
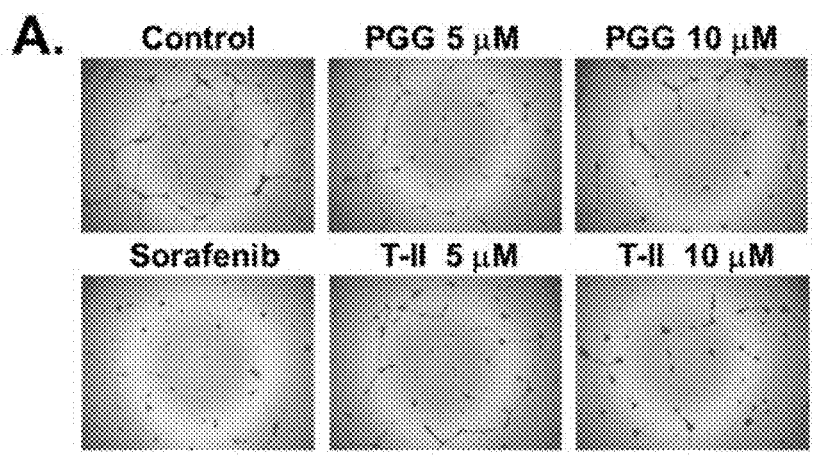
FIG. 3A shows that tellimagrandin II (T-II) inhibits tube formation of human EPCs in a concentration dependent manner without cytotoxic effects.
Figure 3B:
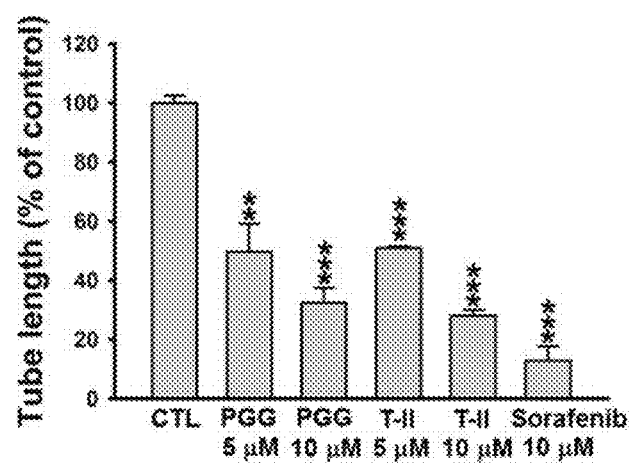
FIG. 3B shows that the release of lactate dehydrogenase is not induced in human EPCs by the described concentration of tellimagrandin II (except 30 μM) at the 24th hour measured by using the lactate dehydrogenase assay. The data of five independent experiments are expressed as the mean±mean standard deviation. As compared with the control group, * means p<0.05;  means p<0.05; * means p<0.001.
Figure 3B:
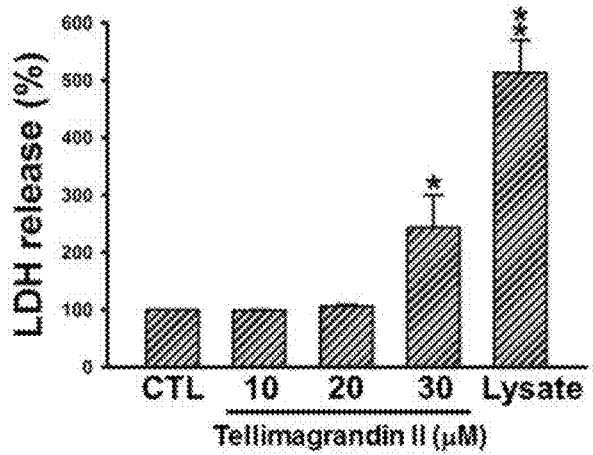
Figure 4:
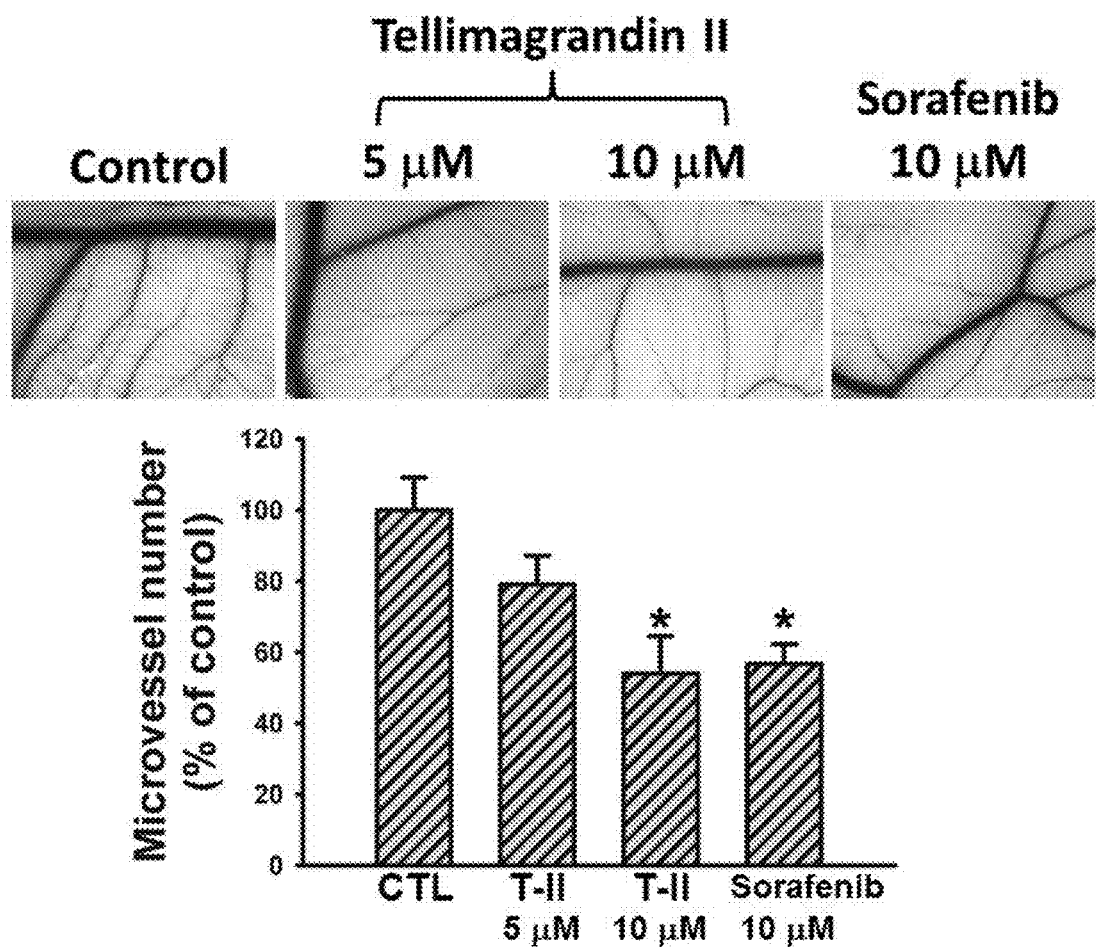
FIG. 4 shows the effect of tellimagrandin II on blocking in vivo angiogenesis by using the chorioallantoic membrane (CAM) assay. Sorafenib is a multiple kinase inhibitor, which is used as a positive control in the in vivo anti-angiogenesis assay.
Figure 5:
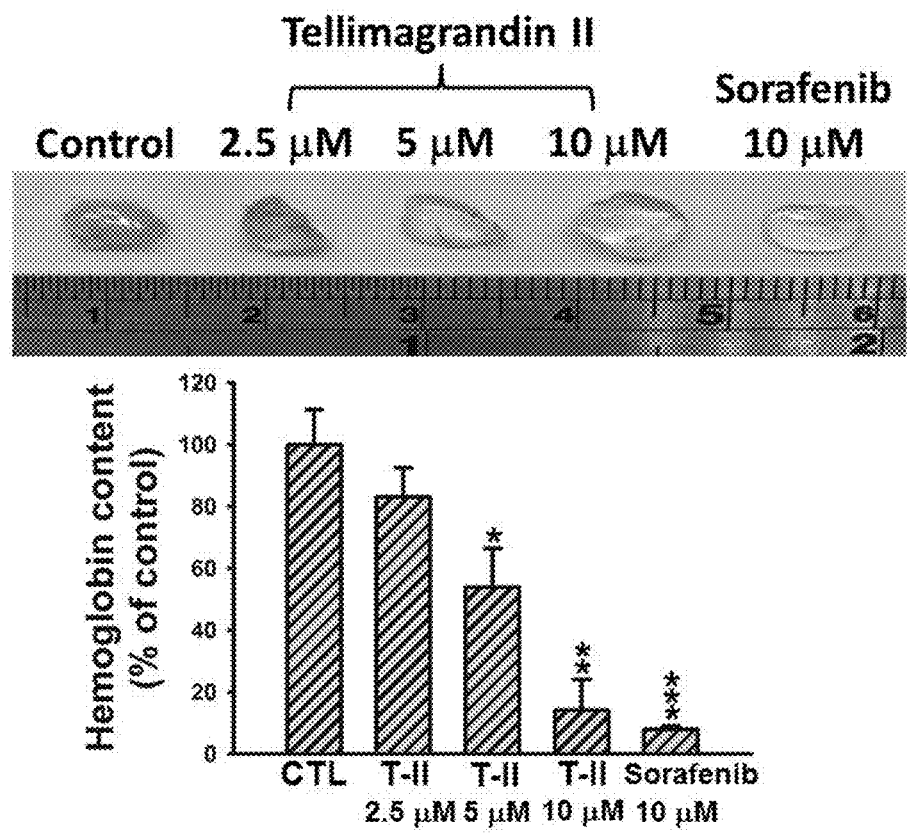
FIG. 5 shows the effect of tellimagrandin II on attenuating capillary formation in the Matrigel plug model. Sorafenib is a multiple kinase inhibitor, which is used as a positive control in the in vivo anti-angiogenesis assay.

*Mitella formosana* (Hayata) Masam. is a perennial herb of Saxifragaceae, a native plant of Taiwan. In the present invention, three kinds of tannin compounds, PGG, tellimagrandin I, and tellimagrandin II, found in the compounds extracted from *Mitella formosana* by using Bioassay-guided fractionation, inhibited the proliferation of EPCs in a concentration dependent manner. As shown in FIG. 2A, in terms of quantity the main compound tellimagrandin II exhibited the most potent effect. The results of tube formation assay confirmed that these three compounds (10 μM) inhibited the tube formation of EPCs in different degrees (FIG. 2B). Moreover, PGG and tellimagrandin II inhibited the tube formation of EPCs in a concentration dependent manner, and the well-known angiogenesis inhibitor sorafenib was used as the positive control in the experiments (FIG. 3A). In addition, when the concentration of tellimagrandin II was 10-20 μM LDH release was not induced, which indicated that the anti-angiogenic effect of tellimagrandin II on EPCs was not caused by cytotoxicity (FIG. 3B). Importantly, CAM-angiogenesis model and mice Matrigel-plus model were used to verify the anti-angiogenic effect of tellimagrandin II in vivo. FIG. 4 shows that tellimagrandin II inhibited in vivo neovascularization in the chicken embryo in a concentration dependent manner. FIG. 5 shows that tellimagrandin II effectively inhibited the formation of capillaries in mice. These results demonstrated that tellimagrandin II was a novel angiogenesis inhibitor by impeding neovascularization of human EPCs.

Prior arts, literatures and studies published before had not disclosed that tellimagrandin I and tellimagrandin II had the anti-angiogenic effect. The present invention demonstrated for the first time that tellimagrandin II had the effect of inhibiting angiogenesis in vitro and in vivo. Given the above, tellimagrandin II, a component of *Mitella formosana*, is unique and has the potential and value to be developed for the treatment of angiogenesis-related diseases.

While the invention has been described and exemplified in sufficient detail for those skilled in this art to make and use it, various alternatives, modifications, and improvements should be apparent without departing from the spirit and scope of the invention.

One skilled in the art readily appreciates that the present invention is well adapted to carry out the objects and obtain the ends and advantages mentioned, as well as those inherent therein. The cells, animals, and processes and methods for producing them are representative of preferred embodiments, are exemplary, and are not intended as limitations on the scope of the invention. Modifications therein and other uses will occur to those skilled in the art. These modifications are encompassed within the spirit of the invention and are defined by the scope of the claims.

What is claimed is:

1. A method of treating a subject suffering from a disease that requires inhibition of neovascularization, comprising administering to the subject a pharmaceutical composition comprising a compound of formula I, wherein the compound of formula I is tellimagrandin II, formula I

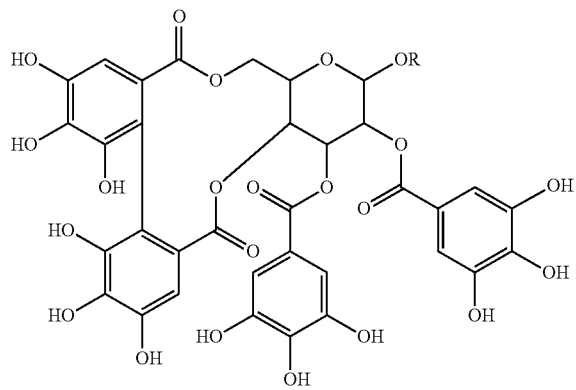

wherein R is

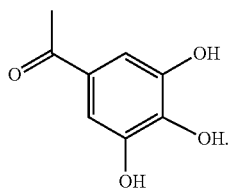

2. The method of claim 1, wherein the pharmaceutical composition inhibits neovascularization in vivo by inhibiting angiogenesis of endothelial progenitor cells.

3. The method of claim 1, wherein the compound of formula I is derived from *Mitella formosana*.

4. The method of claim 1, wherein the pharmaceutical composition further comprises at least one pharmaceutically acceptable carrier, adjuvant or excipient.

* * * * *